United States Patent [19]

Polson

[11] 4,357,272

[45] Nov. 2, 1982

[54] RECOVERING PURIFIED ANTIBODIES FROM EGG YOLK

[75] Inventor: Alfred Polson, Cape Town, South Africa

[73] Assignee: The South African Inventions Development Corporation, Pretoris, South Africa

[21] Appl. No.: 20,786

[22] Filed: Mar. 15, 1979

[30] Foreign Application Priority Data

Mar. 22, 1978 [ZA] South Africa .................. 78/1662

[51] Int. Cl.$^3$ .................. A23J 1/09; A61K 39/00; C07G 7/00; G01N 33/54
[52] U.S. Cl. .................................. 260/112 R
[58] Field of Search .................. 424/8, 12, 85–88, 424/95, 105; 260/112 R, 112 B

[56] References Cited

U.S. PATENT DOCUMENTS

| | | | |
|---|---|---|---|
| 3,415,804 | 12/1968 | Polson | 424/85 |
| 3,819,822 | 6/1974 | Nagal | 424/12 |
| 3,880,989 | 4/1975 | Garcia | 424/85 |
| 3,983,229 | 9/1976 | Relyveld | 424/98 |
| 3,989,818 | 11/1976 | Polson | 424/89 |
| 4,060,597 | 11/1977 | Sato | 424/13 |
| 4,165,370 | 8/1979 | Coval | 424/85 |

OTHER PUBLICATIONS

Goudswaard et al, Poultry Sci., vol. 56, No. 6, Nov. 1977, pp. 1847–1851.
Yamamoto, Biol. Abs. vol. 62, 1976, pp. 2573, Ab. No. 25929.
Aulisio, PSEBM, vol. 131, 1969, pp. 1150–1153.
Williams, Methods in Immunology & Immunochem, Acd. Press NY, vol. 1, 1967, pp. 209–212, 229–237, 244–245.
Stedman, J. of Comparative Path., vol. 79, No. 4, 1969, pp. 507–516.
Yamamoto, Japan J Vet. Res., vol. 23, No. 4, 1975, pp. 131–140.

*Primary Examiner*—Anna P. Fagelson
*Attorney, Agent, or Firm*—Millen & White

[57] ABSTRACT

Immunological preparations are prepared by immunizing hens with an antigen, preferably to a stage of hyperimmunization. The eggs of the immunized hens are collected, the yolk is separated from the eggs, followed by separation of the lipid content of the yolk. The antibodies in the egg yolk are then rendered indispersable with the aid of a water-soluble linear filamentary noncharged polymer precipitant such as PEG and the indispersable antibodies are recovered. This precipitation of antibodies is preferably preceded by a precipitation of caseinaceous proteins at lower polymer concentrations.

The immunological preparations are useful for diagnostic purposes and in appropriate cases also for the treatment of pathological conditions.

13 Claims, No Drawings

RECOVERING PURIFIED ANTIBODIES FROM EGG YOLK

BACKGROUND OF THE INVENTION

The present invention relates to immunological preparations, their manufacture and use.

It is known that birds, e.g. laying hens, transfer their immunity to the yolk of their eggs and thereby to their offspring (F. W. Rogers Brambell "The transmission of passive immunity from mother to young" (1970) North Holland Publishing Company, Amsterdam, London).

The present invention is based on the development of novel or improved techniques for putting this phenomenon to practical use, thereby to achieve a number of novel results and advantages.

In particular it is an object of the invention to produce immunological preparations of satisfactory potency and purity for use as:
 diagnostic agents
 treatment of pathological conditions
 anti-venines.

It is a further object of the invention to improve economics of antibody production by the prolonged recovery of antibody-bearing eggs during the course of the laying period.

It is a further object to produce useful or increased yields of antibodies from antigens of modest to poor immunogenic effectiveness on hens, in particular from antigens of relatively low molecular weight.

It was known to use a class of "precipitants" known as water-soluble, linear, filamentary non-charged polymers for the selective precipitation of proteins, including viruses and serum components, including immunoglobulins (e.g. U.S. Pat. Nos. 3,415,804; 3,989,818, both to Polson).

Thus it is an object of the invention to modify or improve that technique so that it can be applied to the manufacture of immunological preparations, more particularly as set out above.

Further objects, advantages and uses of the invention will become apparent from what follows.

DESCRIPTION OF THE INVENTION

According to one aspect of the present invention, there is provided a process for preparing an immunological preparation which comprises immunising hens against a given antigen, collecting eggs of the hens thus immunised and containing antibodies against such antigen and separating the antibodies from the yolk of the eggs. In accordance with the invention, this is achieved by separating off the lipid content of the egg yolk, rendering the antibodies in the egg yolk indispersable by mixing the egg yolk with a water-soluble linear filamentary non-charged polymer precipitant and recovering the indispersable antibodies separated from the resulting supernatant.

A criterion in selecting the precipitant is that the amount required to "precipitant" for rendering indispersable, must not increase the viscosity of the aqueous medium comprising the egg yolk at the prevailing temperature to a level where it becomes unduly difficult to carry out the process.

Suitable "precipitants" are in particular selected from polyalkylene glycols, for example polyethylene glycol, polypropylene glycol or mixed polymers of ethylene glycol and higher homologues such as propylene glycol or poly-1,4-dihydroxy butaneglycol. Dextran may also be used advantageously. Preferably, in all cases the molecular weight of the precipitant is within the range 2,000 to 30,000.

Examples of other linear filamentary non-charged polymers which, are confirmed by various experiments, can be used but are less preferred at present are nonylphenolethoxylate, polyvinyl alcohol and polyvinyl pyrrolidene.

Because of its ready commercial availability and advantageous properties it is preferred to use polyethylene glycol (PEG) more particular of molecular weight between 2,000 and 30,000, preferably of molecular weight between 4,000 to 9,000, say substantially 6,000. For that reason PEG 6,000 will be stressed in the following.

When using a precipitant other than PEG of M.wt. 6,000 the required amount, equivalent to a known required amount of PEG 6,000, may be calculated in most cases at least approximately from the formula $$\beta = \frac{\overline{V}}{2.303}\left(1 + \frac{r_s}{r_r}\right)^3$$

in which $\beta$ is inversely proportional to the concentration required;
 $V$ = partial specific volume of the polymer;
 $r_r$ = radius of the polymer molecule;
 $r_s$ = radius or stokes radius of the particle to be precipitated.

The theory underlying the above formula is discussed more fully in Biochem et Biophys.Acta. 229 (1971) 535–546.

On inspection of the equation, it would be clear that if $r_r$ be small, $\beta$ the slope of the precipitation curve would be greater, consequently complete separation would occur over a narrow range. This occurs with synthetic organic polymers. When $r_r$ is large, as with dextran, the slope ($\beta$) of the precipitation curve would be less and complete precipitation will occur over a wider range of dextran concentrations. As the excluded volume (which is a function of total length of the polymer molecules) of a thinner polymer is greater than that of a thicker polymer it stands to reason that the thin polymer will produce precipitation of the substance at a lower weight concentration than the polymer of greater diameter would do.

The relationship between required concentration and molecular weight of the precipitant is substantially linear in practice for most cases.

The term "precipitation" and to "precipitate" as used in the present specification, is employed in the colloquial sense in which the expressions are generally used in this art, meaning "sedimentation".

For improved fractionations or purifications it is possible to fractionate a mixture repeatedly, either by repeated fractionation steps in accordance with the present invention or by a combination of such fractionation step with other conventional fractionation steps.

When a polyalkylene glycol, more particularly PEG is used as the precipitant, it is preferred to employ a commercial preparation "polyethylene glycol 6,000", the code number being by approximation indicative of the molecular weight. Thus, polyethylene glycol 6,000 as supplied by Shell is stated by those manufacturers as having an average molecular weight between 6,000 and 7,500, according to the determination methods employed by the manufacturers. In any event the molecular weight of the precipitant is not very critical and minor variations in optimum concentration of PEG due to that parameter are easily determined by a routine experiment, such routine experiment for example, following the general pattern of analogous routine experiments described in our South African Pat. No 63/834, (British Pat. No. 1,006,258; U.S. Pat. No. 3,415,804). Other suitable polyalkylene glycols which may be used instead of or in addition to polyethylene glycol are the polymers of low molecular weight homologues of ethylene glycol, in particular propylene glycol or mixed polymers of polyethylene glycol and such homologues, the preferred molecular weight limits being substantially similar to those described for polyethylene glycol, the upper limits being determined primarily by viscosity considerations.

In accordance with preferred embodiments of the process, the separation of antibodies from the egg yolk involves at least two steps, preferably at progressively increasing conditions of precipitating power of the contents of admixed precipitant as above defined, that is the linear filamentary non-charged polymer precipitant, the initial precipitating power being adjusted to remove easily precipitated impurities, in particular caseinous protein, without precipitating the antibodies, followed by an increase in precipitating power to selectively precipitate the antibodies.

When the precipitant is PEG 6,000, the first precipitation step for removing the caseinous protein should be carried out at more than 3% and less than 4% by weight of PEG 6,000 by weight based on the volume of aqueous yolk. Preferably the yolk is diluted with between one and ten parts, more preferably between 1.5 and 5 parts, preferably 2 parts by volume of water, the water being for example, buffered to a pH of between 6 and 8, e.g. between 6.5 and 7.8, say 7.5.

The correct choice of precipitant concentration during that first precipitation stage is rather critical. Unless the concentration of PEG 6,000 is higher than 3%, the precipitation of caseinous protein may be unsatisfactory, whilst unless said PEG concentration is less than 4%, there may be losses of desired antibody. The preferred concentration of PEG is between 3.3 and 3.7%, more particularly 3.5%.

The second precipitation step, if carried out with PEG 6,000, is found to take place most satisfactorily at concentrations higher than 11% (below which there occurs losses of antibody) and lower than 14%, the concentration at which contaminating substances such as albumen and various undesired proteins are inclined to be coprecipitated. The preferred concentration is between 11.5 and 12.5%, more particularly 12% weight per volume.

The step of lipid removal may take place by extraction with an organic solvent such as toluene. However, a very effective and simple method comprises first mixing the aqueous diluted egg yolk with the amount of linear filamentary non-charged polymer precipitant required for precipitating caseinous protein contained therein and then filtering the resulting supernatant on the surface of which floats the lipid layer, through an absorbent filter plug adapted to retain the lipid layer. An absorbent cotton plug is suitable as such absorbent layer.

According to the aforesaid prior art on determining antibodies in the eggs of immunised hens, the immunisation was not necessarily optimised and the antibodies were determined only in eggs recovered during the period following shortly after the immunisation period.

In accordance with the present invention, immunisation is carried out in progressive steps over a period until the antibody level in the serum of the hen has reached a plateau, and cropping of eggs for antibody recovery is continued over a period of months, preferably 4 months or more, more preferably over the entire or substantially the entire laying period of the hen.

The aforegoing is in itself considered to be a novel aspect of the present invention.

The antibody concentrate obtained by the second precipitation step is preferably subjected to further purification, e.g. by being predissolved in an aqueous medium, followed by renewed precipitation of the antibody, e.g. with alcohol or other suitable protein precipitants, but preferably again with a linear filamentary non-charged polymer precipitant as above defined, e.g. PEG.

For many, if not most purposes the presence of traces of PEG is not considered objectionable. However, if it is objectionable, it is possible to employ a non-objectionable precipitant in the last precipitation stage. Alternatively, if PEG is used for further purification, the immuno globulin concentrate may be freed of PEG by redissolution and precipitation with ammonium sulphate employed at half its saturation concentration.

The temperature at which the process is carried out is not very critical, ranging preferably between 0° and 30° C., more preferably between 4° C. and 25° C., e.g. ordinary room temperature.

The above process is suitable for recovering the antibodies not only in good yields, but also in very pure form, such that in appropriate cases the product can be injected into animals or humans with little or no danger of allergic reactions. It is furthermore believed that, because soft-boiled eggs form such a normal part of human diets, a majority of humans have become desensitised to otherwise allergenic substances present in egg yolk, and which might still be present in trace amounts in the product in accordance with the invention.

Thus, in accordance with one further aspect of the present invention, there is provided a purified injectable form of antibodies recovered from egg yolk.

It is comparatively easy to raise and keep chickens under conditions where they will be exposed substantially only to the antigens against which immunity is desired. It is particularly advantageous that this immunity persists over such long periods, such as the entire laying period without subsequent booster doses of antigen being necessary.

Thus the invention may be applied to the production of anti-venoms, e.g. against snakes, scorpions and spiders. The reduced danger of allergic reactions is a particular advantage, as is the suitability of the process for producing anti-venoms against the rarer species of snakes or snakes against which anti-venoms are not yet readily available from other sources. Particular examples are tree-snakes (boomslang), bird snakes, vine snakes and even mambas.

Such anti-venoms, derived from birds' eggs are considered novel per se.

The invention is also particularly suitable for the manufacture of antibody concentrates for the detection and identification of various antigens in the laboratory, e.g. for pathological or forensic purposes.

The invention may also be applied to the manufacture of polyvalent antivenines.

It is also suggested to employ the invention for the production of anti-foetal proteins for diagnostic purposes in certain malignancies, i.e. liver cancer and other cancers, for the manufacture of anti-lymphocytic sera for use in organ transplantation, anti-foetal proteins for possible treatment of malignancies and all types of anti-sera against any antigens for whatever purpose these anti-sera may be required.

As regards the process it would be within the scope and spirit of the present invention to reverse the sequence of precipitation steps by first precipitating caseinous proteins together with the antibodies at the higher precipitant concentration, followed by lowering the PEG concentration, more particularly by adding aqueous liquid, thereby to redisperse the anti-bodies whilst leaving the caseinous proteins precipitated, and finally if so desired to reprecipitate the anti-bodies from the supernatant.

It has been found that antigens of comparatively low molecular weight, e.g. less than 100,000, and particularly less than 30,000 have a comparatively low effectivity in the production of the desired antibodies in the hen as compared with high molecular antigens of molecular weights greater than 150,000. A preferred feature of the invention provides that the immunogenic properties of comparatively low molecular weight antigens are enhanced by the aggregation of such antigens to immunogenically more effective molecular weights. This is preferably achieved by cross-linking, preferably with glutaraldehyde in the case of basic antigens or with carbo-diimines for cross-linking carboxyl groups on the molecules. Other cross-linking agents may be used.

In this manner it was possible to greatly enhance the immunogenic properties of the antigens of snake venoms. The same procedure is also proposed in accordance with the invention for producing immunological diagnostic agents for the detection of cancer from the respective low molecular weight antigens.

Where the immunological preparations produced in accordance with the present invention are used diagnostically, more particularly where the antigen used in the immunisation of hens is associated with a pathological condition to be diagnosed, the antibodies separated in accordance with the invention, are applied to a pathological test sample and a precipitin reaction between the antibodies produced and the corresponding antigens in the test sample is observed in a manner which may be substantially as known per se. A preferred technique is the well-known Ouchterlony technique, which requires no detailed description, since it is well-known in the literature and from standard textbooks. As a general rule it is preferred for the said technique to be carried out at a substantial sodium chloride concentration in the gel in which the test is carried out, which gel is preferably agarose gel. Suitable sodium chloride concentrations are generally between 0.1 and 0.2 M, usually 0.15 M is preferred which is readily tolerated by the sensitive substances such as viruses. Higher concentrations are used only if no or no satisfactory precipitin reaction is observed in which case the concentration may be used to preferably not exceed 1.5 M. This may yield better reactions with antigens of mol. weights less than 150,000.

A useful description of double diffusion techniques and in particular of the Ouchterlony method can be found in "Methods in Immunology and Immunochemistry" edited by C. H. Williams and Merrill W. Chase, Academic Press (1971), Vol. III, pages 146–161.

Although the above reference recommends the use of either agar or agarose as gel medium for the test, agarose was found to be substantially more suitable in the context of the present invention because of white haloes formed around the yolk immunoglobulin (IgY) wells in agar (possibly due to a reaction product between agaropectin and residual traces of Lysozyme.

In the following the invention will be further described with reference to some preferred examples. For the sake of consistency all examples are carried out using the same precipitant PEG 6000. However, in the light of the preceding description a person skilled in the art can readily apply the examples to different precipitants. The examples are chosen to give a fair and representative cross-section of practical applications of the invention to enable the person skilled in the art to practise different, but analogous embodiments.

EXAMPLE 1

Hens

White Leghorn and Rhode Island Red-White Leghorn hybrids, 20 weeks old, were kept in isolation for immunoglobulin and egg production. They showed no sign of illness or discomfort during the period that they were involved in the experiments.

Chemicals

Polyethylene glycol MW 6,000 daltons (PEG) was used in the fractionation of the egg yolk. Sodium azide at a concentration of 0.1 g/liter was used as a preservative of the washed yolks and of the finally purified yolk immunoglobulin (IgY).

Buffer

The yolks were diluted in 0.01 M phosphate buffer of pH 7.5 which contained 0.1 M NaCl. Buffer of the same composition was used as the dispersion medium for the IgY when finally purified.

Immunisation

The pullets received an initial intramuscular injection with each of the antigens in phosphate buffer of pH 7.5 emulsified with an equal volume of incomplete Freund's adjuvant. The concentration of antigen used was not critical and varied from one antigen to another, but was generally in the range of 1 to 5 mg/ml. After the initial injection the young hens received a further three injections spaced at weekly intervals, each injection had a volume of 1 ml and thus corresponded to between 1 and 5 mg of antigen. A stage of hyperimmunisation was reached Eggs were collected, labelled and stored at 4° until processed for extraction of IgY. This was continued over a period of 9 months.

Extraction and purification of IgY

Several methods for separating the lipoidal matter and casein-like protein from diluted yolk were compared. These involved the use of organic solvents such as ether and toluene and precipitation with ammonium sulphate. Best results were obtained by displacement with PEG.

The method of separation of IgY was remarkable in its simplicity. The yolks collected from a number of eggs were thoroughly washed in a weak jet of distilled water to remove all the albumen. The yolks were dropped into a large glass funnel supported on a measuring cylinder. The fall into the funnel causes the yolk sacks to break and release the yolk which collects in the cylinder. The volume of yolk was measured and a volume of buffer equivalent to two volumes of yolk was added and thoroughly mixed. PEG which had been finely pulverised in a Waring blender was added to a final concentration of 3.5% by weight of polymer to volume of diluted yolk. The mixture was stirred until all the polymer was dissolved. The mixture was centrifuged in a Sorvall centrifuge at 10,000 rpm (12,000×g) for ten minutes. This operation caused the separation of three phases in the centrifuge tubes. These were, a yellow fatty layer on the surface, a clear supernatant layer occupying the largest volume and a semi-solid pliable layer of the bulk of the yolk and caseinous protein "pellet" representing approximately ⅓ of the total volume of substance in the centrifuge tube. The supernatant fluid with the fatty layer was carefully decanted into a funnel containing an absorbent cotton plug in the neck of the funnel. This plug filtered off the lipid layer that was decanted with the supernatant fluid. The volume of the clear filtrate was measured and pulverised PEG was added by gentle stirring to a final polymer concentration of 12 g PEG in 100 ml yolk extract. At this concentration the PEG caused complete displacement of the IgY. A certain percentage of associated proteins notably $\alpha$ and $\beta$ livitin coprecipitated with the IgY. The precipitate was centrifuged off at 10,000 rpm in a Sorvall centrifuge. The pellets were redissolved in the original volume in phosphate buffer and the IgY once more precipitated with 12% pulverised PEG and centrifuged. The pellets obtained were compacted by subjection to a centrifugal force at 10,000 rpm and the exuded solution of PEG originally entrapped in the pellets was removed by suction. The pellets were compacted once more and residual PEG solution discarded. In this manner the polymer which contaminated the IgY was reduced to a level at which it could not interfere with the antibody antigen reaction. The final pellets were dissolved in a volume of phosphate buffer equivalent to half the volume of yolk from which it was derived. The protein concentration in the final product was of the order of 6 mg/ml. Sodium azide (0.01%) was added as a preservative. Sodium azide may also be incorporated earlier, namely in the buffer used for diluting the yolk (see above) in 0.01% concentration. By dissolving the pellets in a smaller volume, more concentrated solutions may be obtained if desired.

Optionally the IgY may be freed of traces of PEG by precipitation of the IgY with half saturated ammonium sulphate followed by centrifugation. The PEG forms a liquid phase in the aqueous ammonium sulphate phase, while the IgY forms a third phase on the bottom of the centrifuge tube.

Rate of introduction of antibodies into the yolk following immunisation

The rate of transfer of antibodies from the hen to the yolk was followed in three systems:

1. $\beta$ Nudaurelia virus-anti $\beta$ Nudaurelia virus IgY,
2. Amandin-anti amandin IgY, and
3. Tetanus toxin-anti tetanus toxin.

Purified IgY isolated from individual eggs laid on alternative days were titrated for their ability to precipitate the antigens in Ouchterlony gel diffusion in the cases of $\beta$ Nudaurelia virus and amandin. The neutralising activity of anti tetanus IgY was tested in Swiss white mice. In all cases it appeared that the antibodies appeared in detectable amounts 10 days after the initial injection. When booster injections of the antigens were given the time lapse between injection and rise in antibody titre became shorter until a level of antibody was reached which remained constant for 4 months. At this stage the experiment was terminated.

The precipitin titre of the IgY directed against $\beta$ Nudaurelia virus was estimated to lie between 1/256 and 1/512 in the yolks of the hen which responded best. The hen which responded poorest showed a titre lying between 1/128 and 1/256.

The yolks of hens immunised with amandin showed maximum precipitating titres of the order of 1/64. This titre can be improved by using the antigen in cross-linked form as described in example 7 below.

Anti-tetanus IgY neutralised 2 mld of tetanus toxin at a dilution of the IgY which varied between $10^{-4}$ and $10^{-5}$. After the injections of the hens had stopped this level of activity was maintained in the yolks for the entire period of the experiment which lasted four months. It was observed as a general rule that the IgY in the egg yolks rises to higher levels than in the hen serum. It has the same molecular weight as in serum (170,000).

EXAMPLE 2

Yolk antibodies (IgY) directed against viruses of plants

Example 1 was repeated using plant viruses as antigens. The appearances of anti plant virus antibody in the yolks followed the same patterns as with Nudaurelia virus, amandin and tetanus toxoid. The titre obtained with IgY against tobacco mosaic virus was of the same order as that usually obtained with antiserum raised in rabbits.

Bromegrass mosaic virus IgY antibodies produced double lines of precipitate in Ouchterlony plates. The lines closest to the antigen well are caused by intact virus particles and the ones near the central antibody well are caused by viral protein subunits.

Turnip yellow mosaic IgY antibodies produced only precipitin lines corresponding to intact virus particles and the titre of the IgY antibodies was similar to the titre of immune sera from rabbits.

Similar results were obtained with Sunn-hemp virus, Broadbean mosaic virus and Cowpea Chlorotic Mottled virus.

The antibody solutions, stabilised with sodium azide can be kept for prolonged periods at 4° C. for use as a diagnostic reagent, employing standard tests, more particularly double diffusion tests of which the Ouchterlony is preferred which is preferably carried out on agarose plates.

EXAMPLE 3

Diagnosis of Bromegrass mosaic virus (BMV)

Bromegrass mosaic virus (BMV) is shown to be present in infected extracts of wheat and barley by the Ouchterlony double diffusion technique in which the IgY type of antibody directed against BMV and produced in accordance with example 2 above, is placed in a well cut into agarose contained in a Petri dish. The test sample of antigen derived from the infected extracts of wheat and barley is placed in wells cut in a circle round the central well and about 5 mm from the central well. 4 to 6 such wells are cut around the central well in the manner well-known from standard literature. The Petri dishes with the reactants in the wells are left at room temperature for 24 to 48 hours. During that period the reactants (namely the diagnostic agent IgY and the BMV antigen of the sample) will diffuse from their respective wells into the surrounding agarose gel to form visible lines of precipitates between the central well and the surrounding wells. These typical precipitate lines confirm the presence of BMV antigen in the test sample, to serve as a positive diagnoses of BMV in the wheat or barley.

Although this is not always necessary, it is a preferred technique to incorporate a concentration of between 0.15 and 1.5 M sodium chloride in the agarose gel which often helps to improve the sensitivity of the test. This is less necessary with viral material than with other types of antigens, particularly those of lower molecular weight. The preferred concentration as a standard technique is 0.15 M (which concentration in the case of viruses is preferably not exceeded). Higher concentrations are preferably selected only if at 0.15 M the observed precipitin response is weak or unobservable.

EXAMPLE 4

IgY antibodies against human IgG

Human and rabbit IgG have a similar low mobility in the electric field and consequently are moved towards the negative pole when subjected to electrophoresis in agarose or agar gel. In contrast, IgY has an appreciably higher mobility towards the positive pole. Because of this difference in mobility, the possibility presented itself of overcoming the difficulties that are found when various antigens of low mobility such as human IgG are analysed by one and two dimensional Laurell electrophoresis. Because of the considerable endosmosis that occurs with IgG, it is necessary prior to electrophoresis to alter the charge on the antibody molecules by chemical reaction. With IgY antibody, such additional chemical modification is not necessary.

It is important in clinical diagnosis to know the level of human IgG in blood circulation. This can be established by the extent to which human serum may be diluted to give a precipitate line against IgY antibody produced in the hen against IgG in accordance with the procedure described in Example 1 and using an antibody preparation extracted from the hen's yolk as described in Example 1.

EXAMPLE 5

Clinical determination of human IgM

It is important in clinical diagnosis to know the level of human IgM. This is an antibody which occurs early during immunisation, especially against bacteria and viruses. Hens are immunised with pure IgM in accordance with the procedure described in Example 1. The IgY antibody against this IgM is recovered from the egg yolks as described in Example 1 and serves as a reagent for the clinical diagnosis using known double diffusion procedures.

EXAMPLE 6

Tetanus antitoxin is prepared by the procedure described in Example 1. The molecular weight of the neurotoxin of Tetanus toxin as produced by the Tetanus organism is of the order of 145,000 and is sufficiently high to produce good antibody yields in hens. Titres of up to $10^{-5}$ mld/ml (minimum lethal dose) with 6 mg IgY/ml are attained. For injection purposes this will be equivalent to the anti-serum conventionally prepared in horses. The IgY recovered from the yolks by the procedure of Example 1 is converted into injectable form as follows:

Traces of PEG are removed from the IgY concentrate by precipitation with 40% alcohol at 0° to 4° C. The IgY precipitate is centrifuged off and freed of alcohol by freeze drying. The resulting powder is then dissolved in the minimum volume of saline. The resulting injectable antitoxin serves as an alternative to horse antitoxin for use in humans who are allergic to horse serum. The dosage is chosen in the same manner as with horse serum antitoxin, depending on the condition of the patient to be treated.

EXAMPLE 7

Snake antivenine (Cobra, Naja Nivea). The venom of this Cobra is composed of at least 20 components, all of which have molecular weights well below 30,000, more particularly in the range between 3,000 to less than 30,000. These components are therefore poor antigens for hens. By cross-linking the venom components with glutaraldehyde, large aggregates are formed through covalent bonding. When these aggregates are injected into hens, they exhibit a higher order of antigenicity. The cross-linkage of the venom components occurs in a random manner, and the different components are represented as antigenic groups on the surfaces of the cross-linked aggregates. Cobra venom is particularly suitable for such cross-linkage as the components are very basic and react well and rapidly with glutaraldehyde in the following procedure:

Between 1 and 10 mg of dried venom is dissolved in 1 ml 0.1 M sodium chloride. Glutaraldehyde is added to a final concentration of 0.6%. The excess glutaraldehyde is dialysed off, using conventional cellophane dialysis tubing. The precipitate is stored for immunisation purposes. The immunisation and recovery of antibody proceeds in accordance with Example 1.

Testing of the antibody product reveals the following: the total antibody titre has been improved by the cross-linking step. However, the antitoxic effect is not yet adequate against some of the 20 or more venom components. The preparation therefor requires to be combined with antivenine concentrates having a selective activity against those additional venom components. An alternative approach is to prefractionate the venom by known techniques (e.g. PEG fractionation, exclusion chromatography) and to prepare antivenines against the individual fractions the techniques being optimised individually for the different fractions) and the different antivenines are then combined in a ratio to produce a preparation effective against the full range of venom components.

EXAMPLE 8

Snake antivenine—Puffadder

Puffadder venom is of less diverse composition than cobra venom (Example 7), the components being moreover of higher molecular weight. After cross-linking as described in Example 7, the resulting antigen preparation can be used in the manner of Example 1 to produce an antivenine preparation.

EXAMPLE 9

Cancer diagnosis

Anticarcino embryonic antigens from human digestive tumours are cross-linked as described in Example 7, and the cross-linked aggregates are used as antigens for the production of IgY antibodies for diagnostic purposes as more fully described in Example 1. In the present example carbodiimide cross-linking agent (concentration 0,1%) is used which cross-links the carboxyl groups of the antigens.

The same procedure is adopted with $\alpha_1$ foetal protein from liver cancer (haepatoma) used in the production of IgY antibody for diagnostic purposes in accordance with the procedure of Example 1. It is necessary to cross-link these antigens as their molecular weights are too low for satisfactory immunological response in the hen.

EXAMPLE 10

Serameba antigen antibodies

Serameba antigen is a mixture of at least 19 antigens and is used for the diagnosis of amoebiasis. The molecular weights of these antigens are low. Accordingly the cross-linking procedure according to Example 7 is adopted before the hens are immunised in accordance with Example 1 for the production and recovery of the antibody preparation.

EXAMPLE 11

Haemocyanin

Haemocyanin antigens of Burnupena cincta have a molecular weight of $8 \times 10^6$ and are directly suitable for the immunisation of hens in accordance with the procedure of Example 1.

The same applies to Haemocyanin antigens of Jasus lalandii, molecular weight $5 \times 10^5$.

Some advantages of the yolk antibody system over the conventional method of production of antisera in mammals are the following:

1. The production of antibodies in the hen and their transfer to the yolks of their eggs continues unabated at a high level of activity once this level has been obtained.
2. The necessity of bleeding and periodic booster injections are obviated, a necessity when conventional laboratory mammals are kept for the purpose of antibody production.
3. The antibody is of the 7 S type and free of IgM. As a result of the method of isolation with polyethylene glycol the antibody is obtained as a single molecular component as shown by analytical ultracentrifugation. The chicken antibody could therefore be advantageous for quantitative determinations by the radical immuno diffusion method. Mixtures of IgM and IgG are known to give erroneous results in this test.
4. As the IgY antibodies are obtained, after the final step in purification, as a semi-solid pellet, it may be dissolved in a small volume of diluent. Hence any desired activity, within limits, may be obtained.
5. The electrophoretic homogeneity of IgY compared to the usual extreme heterogeneity of mammalian IgG could simplify many immunochemical investigations in which purified antibodies are used.
6. Hens are less susceptible to disease than conventional laboratory animals and are housed and fed more economically.
7. Yolk immunoglobulins (IgY) may be extracted from eggs of hens housed on farms specialising in commercial egg production. As hygiene of the housing quarters is of paramount importance as well as the use of hens of the highest production ability, it may be more economical to assign the production of "immune eggs" to such farms rather than to set up an independent poultry unit for the sole purpose of preparing immunological reagents.
8. An additional possibility exists if hens are immunised against snake venoms. The immune IgY may then be used as an alternative to anti-venine produced in horses. This would be a great advantage as a large percentage of people are hyper-sensitive to horse serum proteins. Also, as it requires less antigen to immunise hens than horses, rare anti-venines such as those against the Boomslang and the Bird snake may be produced in sufficient quantity using a relatively small amount of venom.
9. Eggs from immunised hens may be stored at 4° C. for 6 months or longer if desired or required and need only be processed when the antibodies are required. The yolks in a homogenised form and in the presence of sodium azide may be stored at $-20°$ C. virtually indefinitely and the IgY can be extracted when needed.
10. IgY type of antigen against a variety of fowl diseases may, of course also be isolated from the yolks of immunised hens and be used prophylactically in newly hatched or older chicks against diseases which their mothers had not been exposed to yet (examples: Newcastle Disease, other virus diseases and a variety of bacterial diseases). This will protect the chicks passively until they can be immunised actively.

The aforegoing examples involve the use of the most preferred precipitant PEG 6000. However, persons skilled in the art, having due regard to the detailed teachings preceding the examples would have no difficulties in modifying these examples by the analogous substitution of precipitants differing in molecular weight and/or chemical composition.

Specific antibodies may be made from the immune IgY by the recognised methods of affinity chromatography and by absorbing and elution from immuno-precipitates following the method of G. Hardy and M. H. V. van Regenmortel as published in J. Immunological Methods, Vol. 15, 1977, p 305–314. Example: Specific IgY antibody to human IgG was prepared by affinity chromatography. The yield of the specific IgY was 8%. Immuno specific IgY antibody was prepared by dissociation of the complex of IgY and tobacco mosaic virus (TMV) at pH 2.9 in 0.005 M glycine HCl followed by centrifuging to remove the TMV. The total specific IgY isolated represented 18% of the total IgY protein.

What is claimed is:

1. A process for recovering purified IgY antibodies from fowl egg yolk containing said antibodies, comprising the steps of
   (a) rendering the lipid content and the caseinous protein of the egg yolk water-indispersable by mixing the yolk with water and a water-soluble linear filamentary non-charged polymer precipitant in a concentration sufficient to substantially suppress the dispersability of lipids and caseinous protein without substantially suppressing the dispersability of IgY antibodies;
   (b) separating egg yolk substances thus rendered indispersable, including the lipid content, from an aqueous phase which still contains the antibodies dispersed therein; and
   (c) recovering the antibodies from said aqueous phase.

2. A process according to claim 1, wherein the precipitant is selected from the group consisting of polyethylene glycols, polypropylene glycols, mixed polymers of ethylene glycols and higher homologues thereof and poly-1,4-dihydroxy butaneglycol.

3. A process according to claim 1, wherein step (b) comprises separating the precipitated caseinous protein and then filtering the resultant supernatant, on the surface of which floats the lipid layer, through an absorbent filter plug adapted to retain the lipid layer.

4. A process according to claim 1, wherein the precipitant is selected from the group consisting of polyalkylene glycols and dextran.

5. A process according to claim 4, wherein the molecular weight of the precipitant is within the range 2000 to 30,000.

6. A process according to claim 1, wherein the concentration of precipitant in step (a) corresponds to a concentration of more than 3% and less than 4% by weight of polyethylene glycol 6000 based on the volume of aqueous yolk.

7. A process according to claim 6, wherein the yolk is diluted with between 1 and 10 parts by volume of water.

8. A process according to claim 7, wherein the water is buffered to a pH of between 6 and 8.

9. A process according to claim 1, wherein step (c) comprises increasing the concentration of the water-soluble linear filamentary non-charged polymer precipitant to a concentration sufficient to selectively substantially suppress the dispersability of the antibodies, and separating purified substantially homogeneous antibodies thus rendered indispersable from an aqueous phase containing the precipitant.

10. A process according to claim 9, wherein the concentration of precipitant in step (c) corresponds to a concentration of polyethylene glycol 6000 higher than 11% and lower than 14% by weight per volume of aqueous yolk material.

11. A process according to claim 9, wherein in step (a), the diluted egg yolk is buffered at a pH of about 6 to 8, and the polymer concentration corresponds to a precipitating power equal to between 3 and 4% by weight of polyethylene glycol 6000 per volume of aqueous yolk;

and in step (c), the polymer concentration corresponds to a precipitating power equal to between 11 and 14% by weight of polyethylene glycol 6000 per volume of aqueous yolk material.

12. A process according to claim 11, wherein in step (a), the yolk is diluted with between 1.5 and 5 parts by volume of water buffered to a pH between 6.5 and 7.8, and said precipitating power is equal to between 3.3 and 3.7% by weight of polyethylene glycol 6000 per volume of aqueous yolk; and in step (c), said precipitating power is equal to between 11.5 and and 12.5% by weight of polyethylene glycol 6000 per volume of aqueous yolk material.

13. A process according to claim 12, wherein the precipitant is polyethylene glycol with an average molecular weight of from 4,000 to 9,000 daltons.

* * * * *